(12) United States Patent
Mecca et al.

(10) Patent No.: US 7,997,118 B2
(45) Date of Patent: Aug. 16, 2011

(54) SCRUB TESTING DEVICES AND METHODS

(75) Inventors: Jodi M. Mecca, Midland, MI (US); John Keith Harris, Midland, MI (US); Irina V. Graf, Midland, MI (US); Eric Robert Traub, Saginaw, MI (US); Paul L. Morabito, Midland, MI (US); Linda A. Moore, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 285 days.

(21) Appl. No.: 12/239,282

(22) Filed: Sep. 26, 2008

(65) Prior Publication Data

US 2009/0078035 A1    Mar. 26, 2009

Related U.S. Application Data

(60) Provisional application No. 60/960,396, filed on Sep. 26, 2007.

(51) Int. Cl.
*G01N 3/56* (2006.01)
(52) U.S. Cl. .............................................. 73/7
(58) Field of Classification Search ........................ None
See application file for complete search history.

(56) References Cited

U.S. PATENT DOCUMENTS

| | | | | |
|---|---|---|---|---|
| 2,114,831 A | * | 4/1938 | Durfee | 73/7 |
| 4,537,059 A | * | 8/1985 | Sokolovsky | 73/7 |
| 5,557,039 A | * | 9/1996 | Annis et al. | 73/7 |
| 2003/0110827 A1 | * | 6/2003 | Kamitani et al. | 73/7 |
| 2005/0050942 A1 | * | 3/2005 | Schmitt | 73/7 |

OTHER PUBLICATIONS

Chisholm, B., "Combinatorial chemistry methods for coating development III. Development of a high throughput screening method for abrasion resistance: correlation with conventional methods and effects of abrasion mechanism," Progress in Organic Coatings, 47:112-119 (2003).

Presentation by Vratsanos, L.A., Rusak, Michael reported at Athens Conference on Coatings: Science and Technology, Proceedings, 27th, Athern, Greece, Jul. 2-6, 2001 (2001), 435-442. Publisher: (Institute of Materials Science, New Paltz, N.Y.) coden:69CGM9 Titled High throughput screening for latex development in architectural coatings.

Kirsch et al., "Scrub resistance of highly pigmented paints A study on abrasion mechanisms of different scrub techniques," Progress in Organic Coatings, 43:99-110 (2001).

* cited by examiner

*Primary Examiner* — Robert R Raevis
(74) *Attorney, Agent, or Firm* — McDonnell Boehnen Hulbert & Berghoff LLP

(57) ABSTRACT

The invention provides, in one embodiment, a device for performing scrub testing on a plurality of samples simultaneously, including a plurality of scrubbing devices. A stage is provided which positions the plurality of samples in contact with the plurality of scrubbing devices. The scrubbing devices can individually be provided with different weights to produce different forces on the samples. A motion producing device produces one or both of linear and rotational motion between the brushes and the samples. The scrubbing devices are held in the stage so as move freely vertically.

14 Claims, 11 Drawing Sheets

SCRUB TESTING DEVICES AND METHODS

This application claims the benefit of U.S. Provisional Patent Application No. 60/960,396, filed on Sep. 26, 2007.

BACKGROUND OF THE INVENTION

The invention includes scrub testing devices and related methods. Embodiments of the invention are directed to devices and methods related to high throughput scrub testing and the like. Other embodiments of the invention are directed to devices and methods of performing testing and analyzing variables related to scrub testing including evaluation of scrubbing media, e.g., cleaning formulations, abrasive media, and the like; the testing of resistance of coatings to scrubbing with given formulations or media; the testing of scrubber devices or brush materials; stain resistance of materials; and testing the durability of coatings, for example.

Scrub resistance is the ability of paint or a like film or coating of material to resist abrasive cleaning that might remove the paint or film from the surface. Scrub resistance testing is a critically accepted test in the evaluation of the performance of such coating formulations. Scrub testing analysis can also be applied to materials that are not, strictly speaking, coatings, or applied as a film.

The details of standard scrub testing are set out in various testing methods. In North America, for example, scrub testing is defined by two different ASTM methods: D2486 "Scrub Resistance of Interior Latex Flat Wall Paints" and D4213 "Wet Abrasion Resistance of Interior Paints." ASTM D2486 is the most standard protocol used in North America. For ASTM D2486, it is well known that a large number of parameters affect the results of the testing, which create a large variation in test results. Many versions of this test are labor intensive and require constant attention from a human operator.

The device used in the ASTM method can be a standard abrasion tester unit, e.g., a BYK-Gardner™ 'Scrub' Abrasion Tester Model AG-8100, to evaluate the resistance of a material to wear, most commonly a material on a substrate. The material, for example, can be in the form of a solid material, a coating, a composite or a combination of the three. In the standard test, the tester operates by moving a fixture including a brush, sponge or the like, under a constant load, in a linear, reciprocating motion, over the material. Liquids, powders or slurries can be added to the fixture to alter its ability to wear the material. Evaluation of the fixture effectiveness, or alternately the resistance of material to wear, in the presence or absence of additives, is usually monitored as a function of time or number of strokes. Conversely, the unit is also used to assess the ability of the additive to remove the material from the substrate. Therefore, the unit and test is frequently used to evaluate the effectiveness of formulations to clean a substrate. Furthermore, the Gardner™ tester is commonly used in a variety of other tests, such as stain cleaning, stain resistance, scum cleaning, wear testing, adhesion testing, washability, film streaking, and wear resistance.

In a brief example of a standard test, and with reference to ASTM D2486, a coating is applied to a black plastic panel (wet film thickness 0.007 in) and allowed to dry for a set period of time, usually 7 days. The coated panel is then mounted on a linear motion machine like that referred to above, that moves a single nylon brush back and forth over the panel. To accelerate failure, a shim is added under the center of the scrub area, and abrasive scrub media is applied. The machine is stopped when a human operator observes a continuous black line, and the number of cycles observed for the sample being tested to failure is recorded.

As noted above, the test requires a human operator in performing all or many of the steps of the test and monitoring the test. Furthermore, the test is done on one sample at a time, in series, due to the nature of the test unit and the requirement that an operator monitor the test.

Due to the above noted deficiencies of standard scrub testing devices and methods, especially in view of the labor intensive procedure required, there is a demand to develop a high throughput test that would allow for fast and accurate screening of a large number of samples which preferably correlates well to the current method. The invention satisfies the demand. Other limitations of the prior art device and method are also satisfied by the invention as will be detailed herein as well as new investigative applications for such a device.

BRIEF SUMMARY OF THE INVENTION

The invention includes scrubbing related devices and methods that significantly increase testing throughput by testing numerous samples simultaneously or in parallel. In general, embodiments of the invention include devices and methods directed to testing the ability of a material to resist abrasion. In alternate embodiments, the abrasion test is performed with or without scrubbing media. The invention also includes embodiments directed to devices and methods related to evaluating the ability of a media to remove a material from a substrate. The invention also includes embodiments directed to devices and methods for evaluating the ability of a material to resist staining. Embodiments of the invention are directed to parallel or high throughput testing devices. Some embodiments of the invention are directed to evaluations of different media and the use of different media, which can be liquid, solid or combinations thereof, such as solvents, abrasives, staining agents, bleaching agents, carriers and the like.

Some embodiments of the invention are directed to the use of and evaluation of different scrubbing devices also referred to herein as brushes. As used herein, the term scrubbing device or brush will refer to any object that is brought into physical contact against a substrate for the purpose of affecting the coating, soil, or film on the substrate, or used in evaluating scrubbing media and other scrubbing related tests. Accordingly, brushes include objects with bristles, sheets of fabric or pieces of material, sponges or sponge-like material, composite materials, sand paper or sand paper-like materials, plastic, rubber, blades, multi-blade devices, flexible or inflexible, and so on.

Some embodiments of the invention are directed to the use of and evaluation of different loading (mass) levels in the same test. Embodiments of the present invention provide variable stroke lengths, and variations in test motion including linear, circular, random, spinning, orbital motion, and so on.

One embodiment of the invention provides a method of determining the scrub resistance of materials. The method, in general, includes preparing a plurality of samples of one or more materials. The samples of materials are contacted with a corresponding number of scrubbing devices. Relative motion is generated between the scrubbing devices and samples and the samples are analyzed to determine the resistance of the materials to scrubbing.

Another embodiment of the invention provides a method of determining the stain resistance of materials, including preparing a plurality of samples by applying a staining agent to the plurality of samples of one or more materials, applying a staining agent to the materials, and adding one or more scrubbing media to the samples. The plurality of samples of the one or more materials is then contacted with a corresponding number of scrubbing devices. Motion is generated between the scrubbing devices and samples, and the samples are analyzed to determine the resistance of the materials to staining by determining the amount of stain that is removed.

Yet another embodiment of the invention provides a method of determining the efficacy of scrubbing media, including preparing a plurality of samples of one or more materials, the samples including a substrate with one or more test material disposed thereon to be acted upon by the scrubbing media. One or more scrubbing media is added to the samples. The samples are contacted with a corresponding number of scrubbing devices. Motion is generated between the scrubbing devices and samples, and the samples are analyzed to determine the effect of the scrubbing media upon the one or more test material.

Yet another embodiment of the invention provides a method of determining the efficacy of scrubbing devices, including preparing a plurality of samples of material. The samples of material are contacted with a corresponding number of scrubbing devices. Motion is generated between the scrubbing devices and samples, and the samples are analyzed to determine the efficacy of the scrubbing device.

Yet another embodiment of the invention provides a device for performing testing on a plurality of samples simultaneously, including a scrubbing device array including a plurality of scrubbing devices. A stage is provided for holding the plurality of samples in contact with the plurality of scrubbing devices and a motion producing device produces one or both of linear and non-linear motion between the scrubbing devices and the samples.

Embodiments of the invention provide new devices and methods that significantly increase testing throughput by testing numerous samples simultaneously with the additional benefit of incorporation into the system elements, providing automated loading, testing image recording, image analysis and sample unloading. Use of lateral scrubbing coupled with thickness analysis is one preferred method of high throughput scrubbing screening because it has been found that the data correlates well to the standard method.

Reciprocal and lateral scrubbing embodiments of the invention have been detailed herein. Both devices and methods correlate well with the standard testing protocol, while offering higher testing throughput, decreased operator involvement, and opportunity for high-throughput implementation with known ancillary devices. Lateral scrubbing coupled with thickness analysis is a preferred method of high throughput scrubbing screen as presently developed, because the data correlates well to the standard method, and it allows for improved implementation in a mechanical device. The scrubbing screen can be implemented into a larger high throughput workflow that can include automated coating and automated sample analysis such as color and/or thickness measurements.

Furthermore, as the Gardner tester is commonly used in a variety of other tests such as stain cleaning, scum cleaning, wear testing, adhesion testing, washability, and wear resistance, the inventions detailed herein can also be used in similar high throughput screens, testing and evaluation. The lateral scrubbing embodiments detailed herein are highly versatile, allowing the use of different additives, interchangeable fixtures (brushes, sponges, and so on), and various types of substrates (glass, metal, plastic, ceramic, and so on). The shaker table element of the system can work in lateral, as well as other non-linear motion. The devices and methods of the invention permit separation of the substrate into multiple sections, and advantageously allows testing of several different variables, conditions, formulations or soils simultaneously. Users can also use different fixtures, and vary scrubbing forces within the same run.

The methods detailed herein are particularly directed to processing an increased number of samples or performing an increased number of tests over time and can also be directed to use of smaller sample size, and more particularly in a high throughput manner. These, and additional objects, advantages, features and benefits of the invention will become apparent from the following specification.

DETAILED DESCRIPTION OF THE INVENTION

Figure 1:
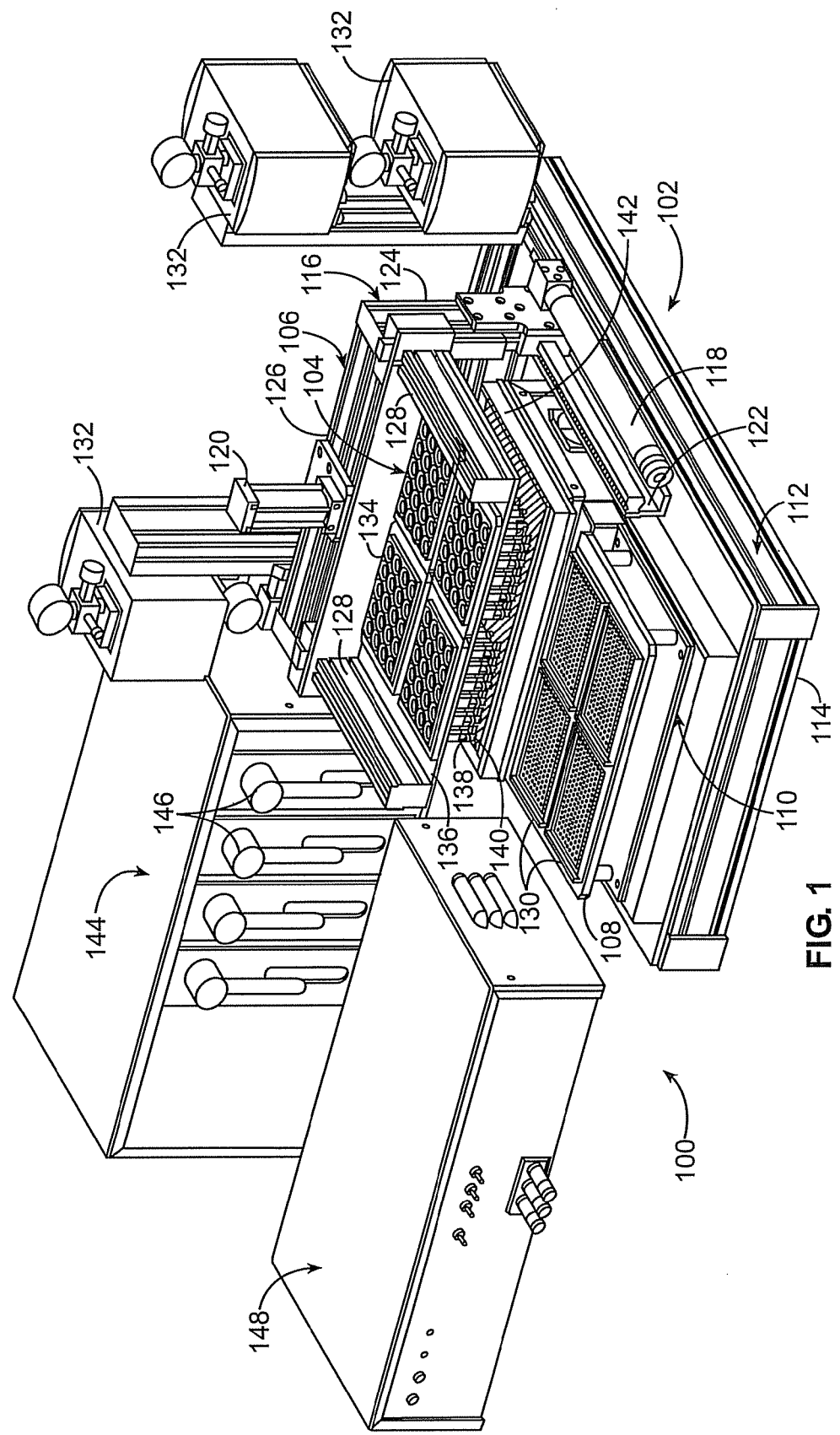
FIG. 1 shows a high throughput scrub testing system according to one embodiment of the invention in a perspective view.

Referring now to the drawings, FIG. 1 illustrates one embodiment of a system 100 for performing scrub-related testing according to the invention. It will be understood that the system 100 can take different forms from that depicted, some embodiments of which will be described hereinbelow. Embodiments of the invention, which will be described below in more detail, are directed to providing high throughput capability to abrasion or scrub testing and related methods. It will be understood that sample preparation for the following devices and methods can be performed by a device having automated functions for high efficiency sample preparation.

The system 100 shown includes a scrubber assembly 102. The scrubber assembly 102 generally includes a brush array 104 disposed on a movable stage 106. The scrubber assembly 102 also includes a sample holder 108. The sample holder 108 is positioned on and fastened to a motion producing device, preferably a shaker table 110. Main elements of the scrubber assembly are disposed on a scrubber assembly frame 112.

The scrubber assembly frame 112 can be any arrangement of frame members, parts and plates, shown generally at 114 that suitably support the elements of the scrubber assembly 102. The frame members 114 in the present embodiment include extruded aluminum beams connected into a rectangular arrangement. It will be understood that assembly of a suitable frame from such members is completed with well known techniques.

The movable stage 106 is any arrangement of frame members, parts and plates, shown generally at 116, which movably support the brush array 104. As shown, the stage 106 includes a pair of spaced lower members 122 (one shown) connected to a pair of spaced vertical members 124 (one shown). The pair of spaced vertical members 124 are connected by a span member 126 at top ends thereof. Each of the pair of spaced vertical members 124 includes a horizontal arm member 128 extending from the span member 126. The horizontal arm members 128 hold the brush array 104. Other suitable arrangements of frame members are contemplated by the invention. It will be understood that an objective of the frame members and other elements of the system 100 is to provide brushes in an array that allows for parallel scrubbing of a corresponding array of samples.

Movement of the stage 106 can be effected by one or more pneumatic cylinders 118 arranged to move the moving stage in a horizontal direction. In this embodiment, one end of cylinder 118 is attached to the scrubber assembly frame 112 and the other end of the cylinder is attached to the moving stage 106. Any suitable means of providing motion to the stage 106 is contemplated. The position illustrated can be considered a starting position. While automated movement of the moving stage 106 is preferred, movements can be performed by an operator manually, for example, or other means.

The stage 106 can be provided with a vertical actuator 120 positioned on the span member 126. The vertical actuator 120 raises and lowers the brush array 104 in a vertical direction. The vertical actuator 120 can be a pneumatic cylinder or an electrical servo motor or the like, capable of raising and lowering the brush array 104 accurately. Moving the brush array 104 from the starting position to a position over the sample holder 108 can be considered an end position, a test position or the like.

The shaker table or motion producing device 110 functions to impart movement to the sample holder 108. While the shaker table 110 can function to produce circular, orbital, random or other motion, preferably the shaker table produces linear, reciprocating motion. It will be understood that the invention contemplates producing a desired motion between the brush array 104 and samples in the sample holder 108. This can be accomplished by either moving the sample holder 108 or the brush array 104, or both.

The sample holder 108, as shown, includes a platform on the shaker table 110 and includes four positions for receiving sample trays 130. The sample trays 130 can be held in place by vacuum, for example, although it will be understood that any method for fixing the trays 130 can be employed. As some of the samples contemplated for testing in the illustrated device are thin, and clamping might prove difficult, vacuum holding of the samples is considered preferable. In addition, vacuum hold devices permit quick sample changeovers and enhances the throughput functionality of the invention. Vacuum pumps 132 are shown positioned on the scrubber assembly frame 112, but can be positioned anywhere in operative proximity to the system scrubber assembly 102.

The brush array 104 includes four brush holder plates 134, but can hold more or less than four plates. Generally, each of the brush holder plates 134 is a flat plate, adapted to fit into spaces (not shown) on a brush array plate holder 136 of the brush array 104 and connect thereto. Each of the brush holder plates 134 hold a plurality of scrub device holders 138, alternately brush holders. In the example shown, each of the brush holder plates holds 24 brush holders 138, but other numbers are contemplated. The brush holders 138 are slidably disposed in the plates 134 to move vertically in the brush holder plates 134. The holders 138 are permitted to move vertically at least to adapt the operation of the brushes 140 to different thickness of substrates and/or samples or to wearing of the brush. Each brush holder 138 includes a scrub device 140, and in this embodiment the scrub device includes a brush. More details regarding the brush holders 138 and brushes 140 will be provided hereinbelow, but it will be understood that the brushes can be objects with bristles, sheets of fabric or pieces of material, composite materials, plastic, rubber, blades, multi-blade devices, and sandpaper, abrasives incorporated onto or into a fabric, flexible or inflexible, and so on.

The brush holders 138 are preferably hollow to accept weights or a material for adjusting the force applied by each combined brush 140 and brush holder 138. In this manner, each brush 140 can be provided with different weight if the test calls for varying the weights of the brushes and the scrubbing force on a substrate. While adding weight to each brush holder 138 is the preferred mechanism for adjusting the force between each brush 140 and a surface upon which the brushes bear, other mechanisms can be used, such as springs, air pressure, fluid pressure or any suitable method of providing a bias or force to each brush. The brush holders 138 can be provided in predetermined weights according to a desired test specification. Thus, the brush holders 138 can be solid rods, semi-solid and/or made of materials to achieve the desired weight.

The force which each brush 140 applies to a corresponding test sample area can be from 15-300 grams in one example. Each brush holder 138 can be a hollow tube, cylindrical or rectangular in radial cross-section and attached in a manner which permits free movement in the vertical direction, so that the weight of the holder and the additional weight (if any) added to the holder is applied vertically to an attached brush and thus, applied to the sample. The force provided by the mass of the holder 138 can be increased by adding weights in the desired amount to each brush holder. Also, higher weight, e.g., 500 grams or more can be desired depending on the coating being tested and other conditions or the tests being performed.

The brush array 104 is positioned, at a start position shown, above a conditioning station 142. The conditioning station 142 is a fluid bath or pan used contain a conditioning material to condition the brushes 140. Conditioning of the brushes is a common first step of performing scrub-related tests. As discussed above, conditioning of brushes can be done with water and other well-known conditioning media as is known in the art. The brushes 140 can also be exposed to a cleaning solvent while in the start position.

Also shown in this embodiment is a fluid media delivery system 144. The media delivery system includes a pump system, preferably one or more syringe pump 146, for accurately delivering predetermined amounts of fluid scrubbing media to a position under or near each brush and the samples. It will be understood that the media delivered can be any of a large selection of media related to performing scrubbing related tests on the system 102 of the invention. For example, the media can be water, Leneta SC-2, scrubbing solutions, any suitable solvent, stain removers, surfactant solutions, cleaning solutions, bleaching agents, laundry pre-treatment solutions, floor wax strippers, abrasive solutions or materials, and the like and combinations thereof. Media delivered to the samples being tested can be any suitable amount, and can be, for example, in the range from 5-5000 uL, per sample tray 130.

A controller 148 is provided for electrical and pneumatic control of the scrubber assembly 102 and fluid media delivery system 144. The controller 148 includes well known circuitry and mechanisms for timing the length of the scrubbing operation, movement of the moving stage 106, operation of the vacuum pumps 132 and so on.

The controller 148 can operate in either or both of two modes; a manual mode and an automated mode. The manual mode is designed to allow users to operate the scrubber in sequence of steps by directly manipulating controls on the controller (not shown). The automated mode allows for the addition of a computer (not shown) to automatically run a sequence of steps in more of an unattended fashion compared to the manual mode. Both modes can perform similar mechanical steps (see below) but the automated mode feature can be adapted for the addition of a robotic feeder (not shown), the ability to use standard HT software, and the ability to use syringes, for example, to add cleaning solution during a run.

The manual mode does not require the use of a computer to operate. In this mode, the following operations can be performed manually: the system 100 and/or scrubber assembly 102 can be turned on and off; the speed can be controlled by manual adjustment of, for example, a variable potentiometer with a numerical readout; the raising and lowering of brushes can be manually effected, and; the movement of brushes can be moved from a scrub position to a home position (which is the wash position).

In an automated mode the system 100 and/or scrubber assembly 102 are connected to a computer (not shown) for unattended automated scrubbing and enables automated features such as: on/off control of the system 100 and/or scrubber assembly 102; control of speed by allowing for variable shaker speed or selection of a number of preset shaker speeds; control of raising and lowering of brushes; control of the movement of brushes from the scrub position to the home position (which is the wash position); allows for the use of standard HT software to run the system and send information to a database; allows for automated dispensing of cleaning solution onto the surface when scrubbing (i.e. controls the syringes to add cleaning solution); allows for the addition of and control of a robot to feed samples to the scrubber and any pre- or post-treatment of the materials (i.e., washing or drying the scrubbed material).

Figure 2:
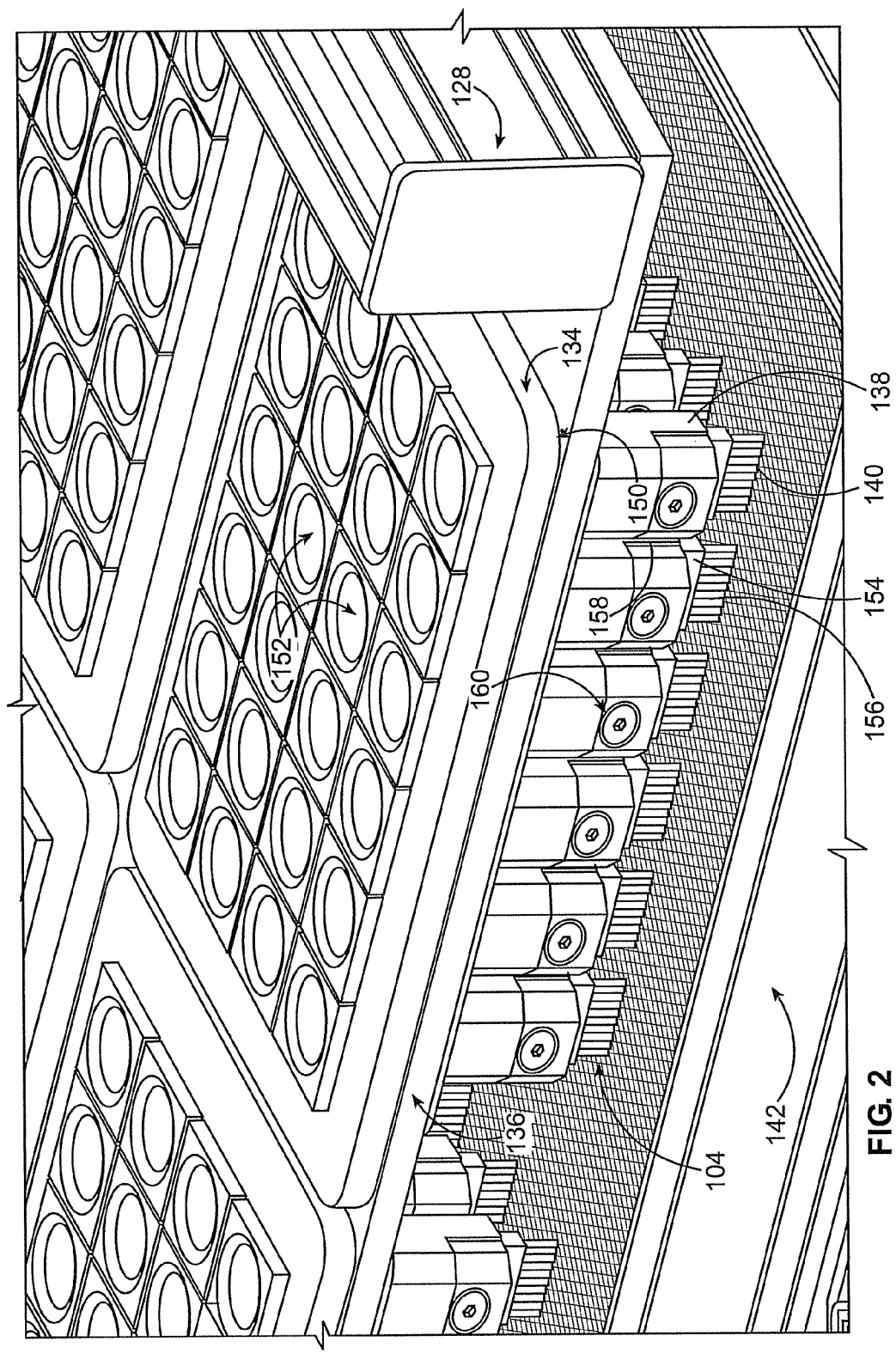
FIG. 2 shows a partial perspective view of a brush array according to the embodiment of the invention shown in FIG. 1.

FIG. 2 shows the brush array 104 including a brush holder plate 134. Each of the brush holder plates 134 includes a flat plate, adapted to fit into an opening (not shown) on a brush array plate holder 136 of the brush array 104 (see FIG. 1) and connect thereto with suitable fasteners (not shown) which can be screws or equivalents thereof. Each of the plates 134 includes a number of openings (not shown) corresponding to the number of brush holders 138 desired to be held simultaneously.

Each of the brush holder plates 134 hold a plurality of brush holders 138. In the example shown each of the brush holder plates holds 24 brush holders, but other numbers are contemplated. A top part of each brush holder 138 is open in this embodiment, to a hollow interior defining a well 152. Each well 152 is preferably sized and shaped to receive one or more weight or a mass of material (not shown) to provide a down force to each brush holder 138.

The brush holders 138 are permitted to move vertically in the brush holder plates 134. The holders 138 are permitted to move vertically at least to adapt the operation of the brushes 140 to different thickness of substrates and/or samples. Each brush holder 138 includes a brush 140. Each brush 140, as shown in the present embodiment, includes a rectangular body portion 154 and a rectangular line or group of brush bristles 156. The brush body 154 is held captive in a receiving slot 158 in the end of the brush holder 138 opposite the top open end. In the figure shown, the mechanism for holding the brush body 154 is a screw and plate 160 assembly which holds the body in the receiving slot 158.

Figure 3:
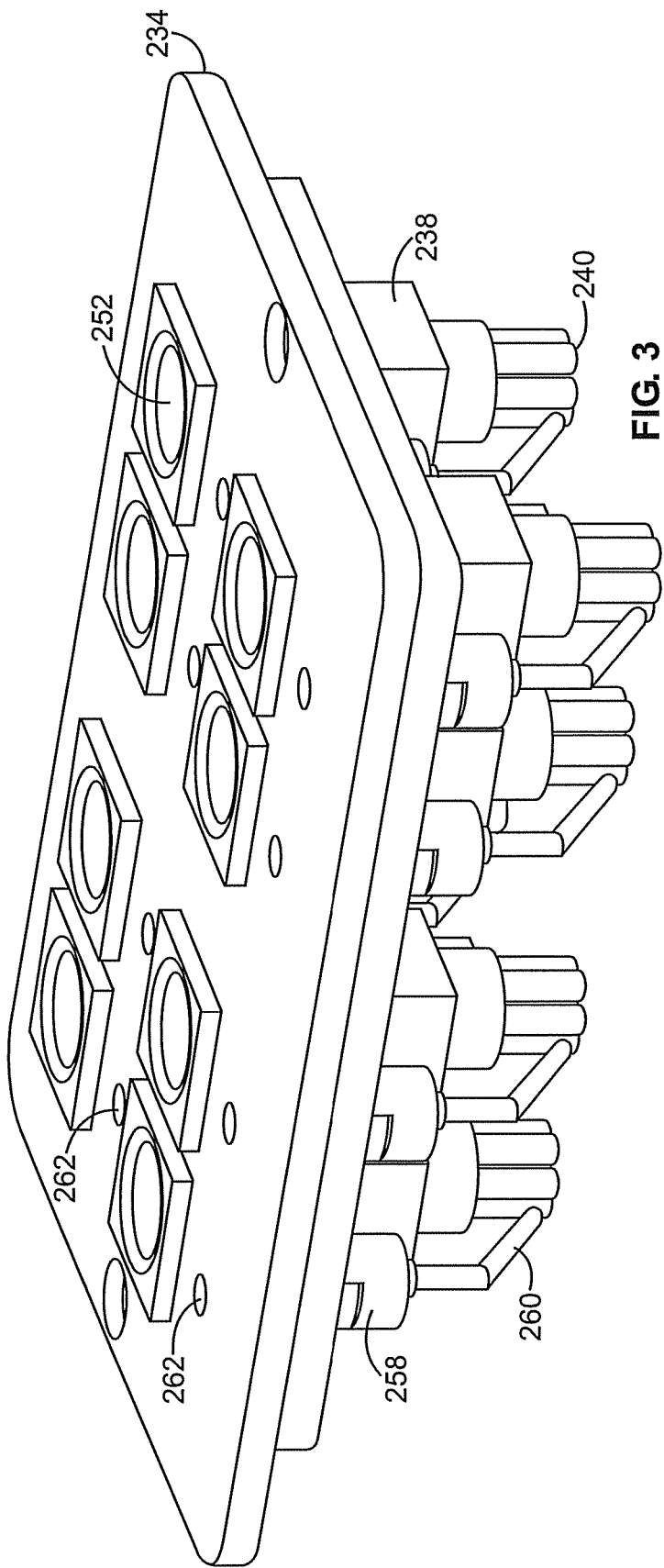
FIG. 3 shows a brush holder plate with brushes and fluid conduit according to another embodiment of the invention.

FIG. 3 shows a brush holder plate 234 holding 8 brush holders 238. The brush holders 238 are similar to the holders shown in FIG. 2, in that the upper ends include an opening and hollow interior defining a well 252 in each holder. The lower ends of the brush holders receive brushes 240 by threaded engagement. Adjacent each of the brushes 240 is a fluid conduit 258 and nozzle 260 for directing fluids, such as the various categories of media discussed herein. The plate 234 includes passageways 262 each respectively in fluid communication with the fluid conduit 258 and nozzle 260. The passageways 262 are sized and shaped to connect to tubing (not shown) from the fluid pumps 146 (see FIG. 1). In this manner, fluid/media is delivered to each of the brushes 240 and dispensed as desired with respect to rate and amount.

Figure 4:
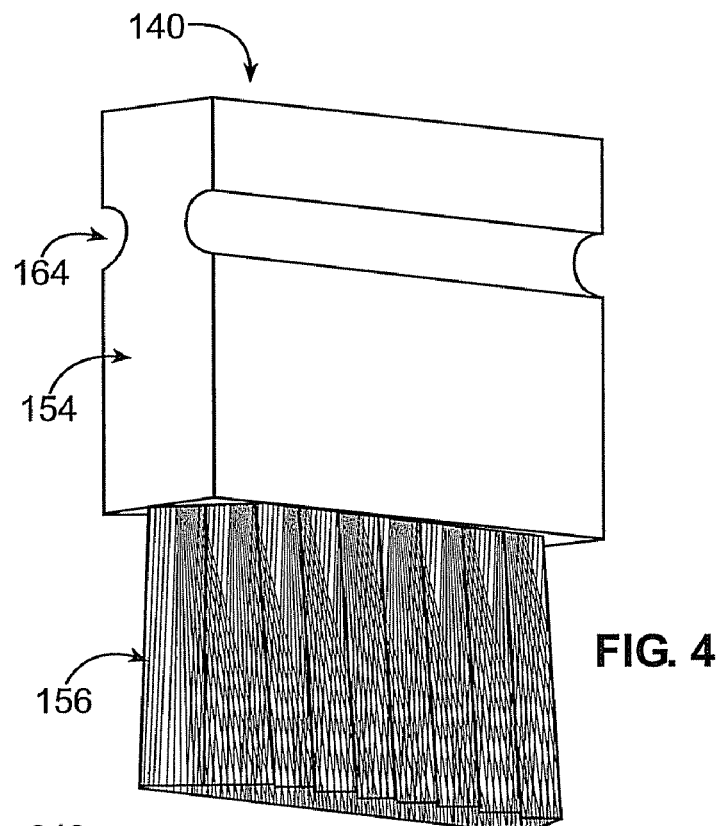
FIG. 4 shows a perspective view of a brush according to an embodiment of the invention.

FIG. 4 shows an embodiment of a brush 140 including a brush body 154. The brush body 154 includes a feature for attaching the brush 140 to a brush holder 138 (see FIG. 1). In this example, the feature is a pair of matching horizontal grooves 164 in the sides of the body 154. The brush 140 includes a plurality of bristles, or grouped bristles 156.

Figure 5:
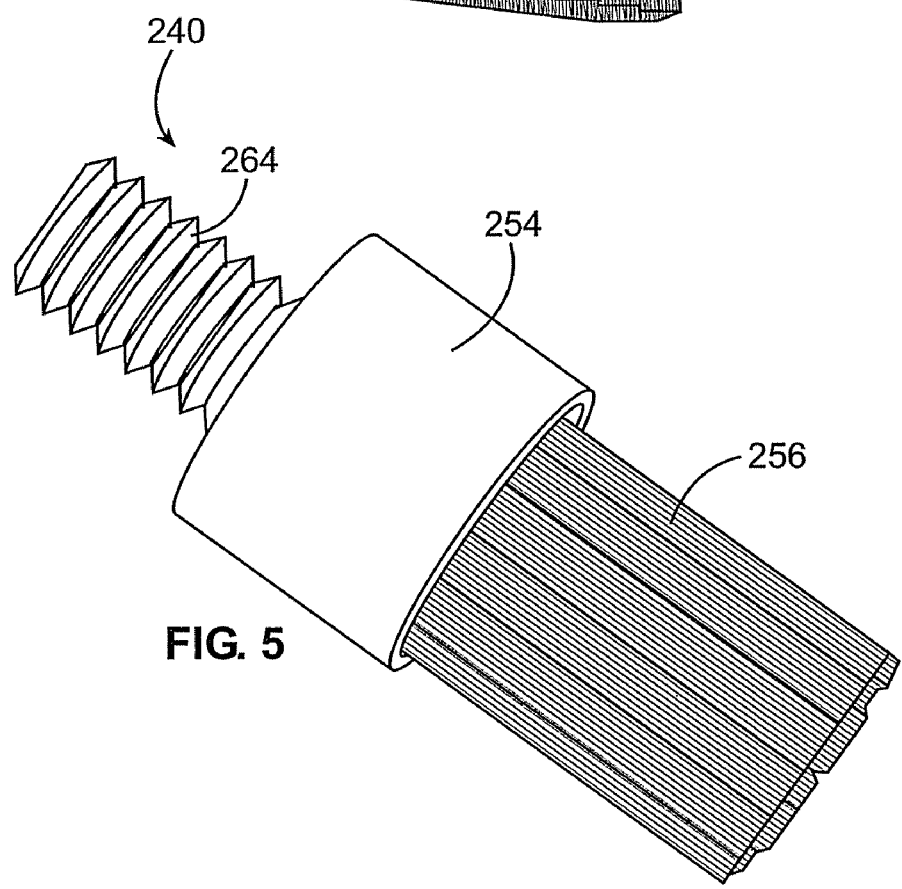
FIG. 5 shows a perspective view of a brush according to another embodiment of the invention.

FIG. 5 shows an embodiment of a brush 240 including a brush body 254. The brush body 254 includes a feature for attaching the brush 240 to a brush holder 238 (see FIG. 3). In this example, the feature is a threaded rod 264 extending from the top of the body 154. The brush 240 includes a plurality of bristles, or grouped bristles 256.

The size of each brush 140, 240 is preferably smaller than the area of each individual sample for which the brush is designed to be used. For example, the contact area of the brush can be from about 5 percent to about 75 percent of the sample area. The sample area can range, for example, from about 25-500 $mm^2$ (square millimeters). Preferably the sample area is 150-200 $mm^2$. However, it will be understood that other sample sizes can be preferred depending on the specific circumstances of the test, for example, related to the sample material or area and the brush material, or the scrub media being used.

While the size of the brush 140, 240 is not critical, a relatively small size brush is desired to maximize the number of samples being tested in an apparatus having a plurality of samples and brushes as will be shown below. It will be understood therefore, that the brush size will be provided in a size sufficient to obtain satisfactory and repeatable action on a sample and accordingly can be somewhat less than the area of a sample to be tested.

One specific example of a brush 240 (see FIG. 5) includes an aluminum body or base 254 sized ½"×¼" (diameter× height). Each brush 254 includes 0.010" black level 6.6 nylon fill bristles, at a 15 mm (0.5905") trim out, and having seven individual tufts 252 being about 0.1-0.125" in diameter each. The tufts are arranged in a circular pattern of six tufts 254 surrounding at an equal distance about a central tuft 256. The circular pattern is about 0.32" in diameter on the 0.5" diameter body. A desired sample size for such a brush can have an area about ¾"×¾". It will be understood that other sizes, shapes, and configurations of brushes and brush tufts can be used in the apparatus of the invention, so long as they are capable of producing abrasion to samples being tested sufficient to distinguish between experimental variables across the samples.

In use, an array of samples can be prepared in a method consistent with standard ASTM method or according to any desirable method. To summarize one such sample preparation method, a solution of scrub media in water can be prepared by combining standardized abrasive type scrub medium (Leneta SC-2) and water at a standard ratio or a modified ratio depending upon the desire of the tester. The coating formulations can be drawn down side by side on Leneta Scrub Test panels with a drawdown bar having a gap of 7 millimeters. The panels are preferably allowed to dry at 50% relative humidity and 25° C. for seven days before being evaluated.

Figure 6:
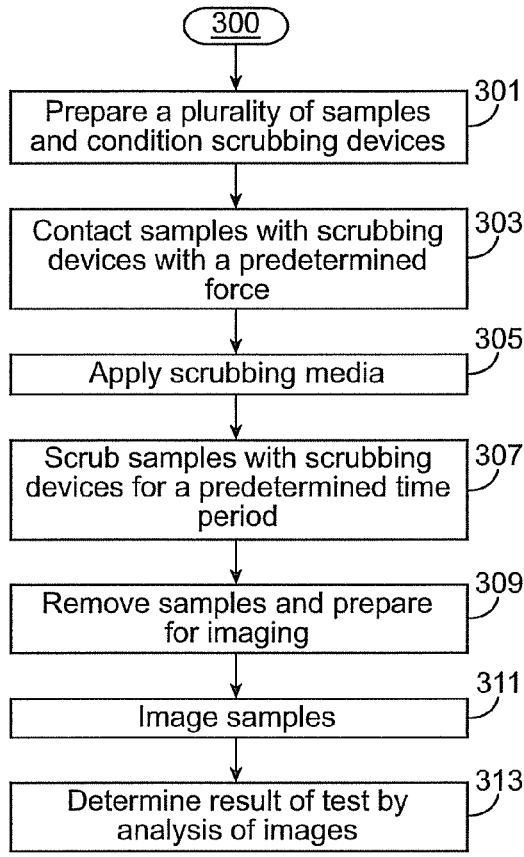
FIG. 6 shows a method of testing scrub resistance according to one embodiment of the invention.

Referring back to FIG. 1 and FIG. 6, an example of a method of testing scrub or wear resistance 300 is shown. Prior to testing, brushes 140 are conditioned 301 by soaking in a conditioning material in the conditioning station 142. The conditioning fluid can be water or another suitable fluid. The brushes 140 can be conditioned for one day or a different amount of time depending on the coating being tested and other variables.

Samples to be tested are arranged on the sample holder 108 and held by activating the vacuum pump(s) 132. The movable stage 106 is moved over and is lowered into contact 303 with the samples held on the sample holder. In the alternate, samples can be elevated towards the brushes 140.

In operation the shaker unit 110 can be activated before or preferably after contact is made between the brushes 140 and samples. The shaker unit 110 is operated for a predetermined time, e.g., a set number of minutes from the time the motion of the unit 110 is in contact with the sample. The time samples are scrubbed depends on many factors, for example, the abrasion resistance of the sample, the abrasiveness of the brushes 140 or other scrubbing device, the properties of the scrubbing media (which can be adjusted with different materials or material percentages to change the abrasiveness or solvent activity), the thickness of the sample coating and the force between the sample and brushes, for example.

Scrub media, for example, 0.2 mL (milliliters) of scrub media (Leneta SC-2 and water at a ratio of 7:5) is added to the sample area 305 manually or automatically by the fluid media delivery system 144. Additional aliquots of scrub media can be added continuously or at intervals during the scrubbing experiment.

The sample 106 is scrubbed, for example, for a set amount of time 307. The shaker table 110 is set, for example, at a predetermined rate of 140 cycles/minute and travel length of 10 mm. The force between the brushes 140 and samples can be set at 290 grams, which is the weight of the brush/brush holder and additional weight. At the end of the predetermined time, which preferably is a period of time sufficient to produce enough wear on at least one of the samples being tested and to distinguish between experimental variables across the samples, the samples are removed from the scrubber apparatus 102. The samples are wiped, for example with a damp sponge or the like, to remove residual scrub media and allowed to dry 309. Two or more duplicate measurements can be performed for each sample.

The samples can then be imaged 311. Any suitable imaging device (not shown) is contemplated. The image thus produced is processed and analyzed to determine how much material has been removed from the samples. Generally speaking, the less area of material that has been removed from the particular sample, the greater the abrasion resistance of the sample material or formulation.

According to the above, samples prepared and processed as described herein are imaged using, for example, a standard office scanner using full color scale. It will be understood that any device capable of imaging the tested samples can be used. As an example, the scanned images are preferably analyzed 313 using Image® software (available at http://rsb.info.nih-.gov/ij/) by converting the images to black and white using a common threshold value of 170 and then computing the fraction of black and white in a rectangular region of interest.

Samples are analyzed with image analyses and in the alternate, also with thickness analyses. Samples processed by the invention can also be analyzed using a thickness-measuring gauge, for example with a Mitutoyo IDC digimatic indicator (resolution=0.00005", measuring range =0-0.5"). The region of the coated substrate that did not have coating of paint can be used to set thickness at zero. The difference between the thickness of the un-scrubbed area and most scrubbed-off area (located in the center of the scrubbed area) is measured to determine the thickness of the coating on the panel.

Figure 7:
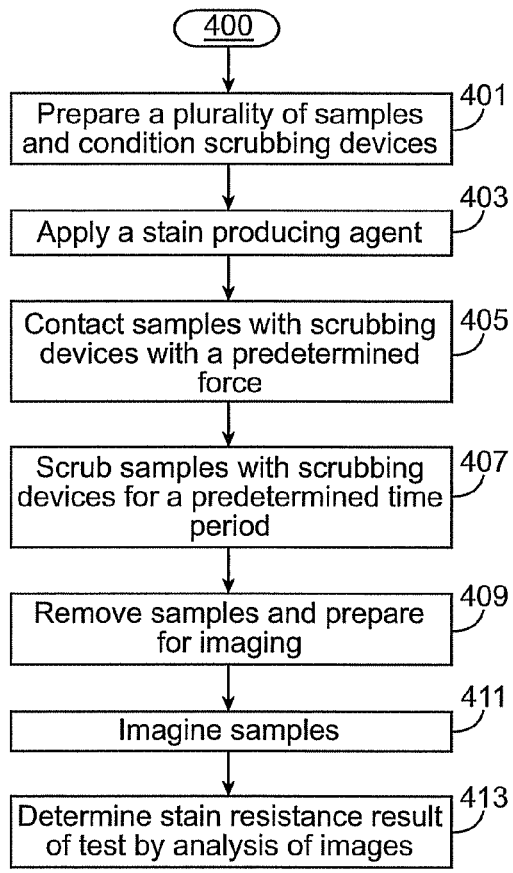
FIG. 7 shows a method of testing stain resistance according to one embodiment of the invention.

FIG. 7 illustrates, generally, a method 400 of analyzing stain resistance of various substrates, coatings and/or materials. It will be understood that many of the steps detailed in the discussion of the method shown in FIG. 6 apply to the following method. Referring back to FIG. 1, prior to testing, brushes, in the form of sponges 140 are conditioned 401 by soaking in a conditioning material in the conditioning station 142. The conditioning fluid can be water or another suitable fluid. The sponges 140 can be conditioned for one day or a different amount of time depending on the coating being tested and other variables. The sponges 140 can be further conditioned 401 by moving the brush (i.e., scrubbing) on a surface with a scrub media solution, in the form of a cleaning solution, for 2 minutes, for example. The sponges 140 are then rinsed by rinsing in water (or a suitable alternate fluid) for approximately 5 minutes. Of course, other conditioning sequences can be used.

A staining agent is applied to samples to be tested 403. In this example, the samples can be a substrate with various coatings, films, or materials applied thereon for testing the resistance of the coating to materials which can produce stains (a staining agent), which can be, for example, oil, foods, tannic acid, colorings, soil, and the like. The samples are arranged on the sample holder 108 and held by activating the vacuum pump(s) 132. The movable stage 106 is moved over and is lowered into contact 405 with the samples held on the sample holder. In the alternate, samples can be elevated towards the brushes 140.

In operation the shaker unit 110 can be activated before or preferably after contact is made between the brushes 140 and samples. The shaker unit 110 is operated for a predetermined time, e.g., a set number of minutes from the time the motion of the unit 110 is in contact with the sample.

Scrubbing media (particularly a stain removing media) is added to the sample area 403 manually or automatically before being added to the station 142. The sample 106 is scrubbed, for example, for a set amount of time 407. The shaker table 110 is set, for example, at a predetermined rate of 140 cycles/min and travel length of 10 mm. The force between the sponges 140 and samples can be set at 145 grams, for example, which is the weight of the sponge/brush holder and additional weight. At the end of the predetermined time, which preferably is a period of time sufficient to produce enough staining on at least one of the samples being tested and to distinguish between experimental variables across the samples, the samples are removed from the scrubber apparatus 102. The samples are wiped, for example with a damp sponge or the like, to remove residual scrub media and allowed to dry 409. Two or more duplicate measurements can be performed for each sample.

The samples can then be imaged 411 as detailed above. The images thus produced are processed and analyzed to determine the extent of stain resistance shown by the various samples.

Figure 8:
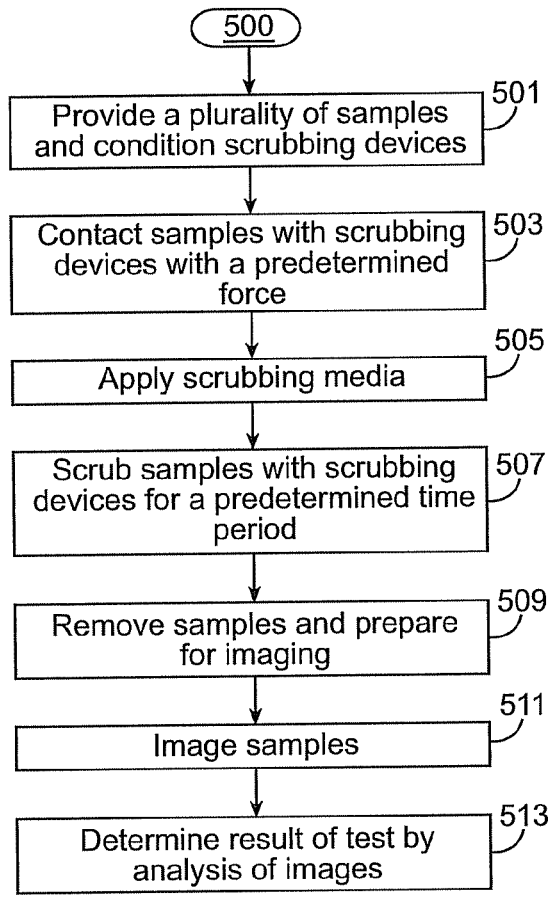
FIG. 8 shows a method of testing scrub media according to another embodiment of the invention.

FIG. 8 illustrates, generally, one embodiment of a method 500 of testing the efficacy of various scrubbing media in removing stains, soil, floor wax, grease, and other materials from a substrate, coating, film or the like. Steps detailed in the discussion of the method shown in FIG. 6 can apply to the following method. In this example, the scrubbing media can be any media or combinations thereof, for example, organic and/or aqueous based solvents, cleaning fluids, soil removers, bleaching agents and the like; surfactants; abrasives; and any other suitable media.

Referring back to FIG. 1 and prior to testing, brushes 140 are conditioned 501 by soaking in a conditioning material in the conditioning station 142. The brushes 140 can be further conditioned 501 by moving the brush (i.e., scrubbing) on a surface with a scrub media solution. The brushes 140 are then rinsed by rinsing in water (or a suitable alternate fluid) for approximately 5 minutes. Of course, other conditioning sequences can be used.

Samples to be tested are arranged on the sample holder 108 and held by activating the vacuum pump(s) 132. In this example, the samples include some material which investigators are interested in studying the removal thereof from a substrate or coating or the like.

The movable stage 106 is moved over and is lowered into contact 503 with the samples held on the sample holder. In the alternate, samples can be elevated towards the brushes 140. In operation the shaker unit 110 can be activated before or preferably after contact is made between the brushes 140 and samples. The shaker unit 110 is operated for a predetermined time, e.g., a set number of minutes from the time the motion of the unit 110 is in contact with the samples.

A scrubbing media is added to the sample area 505 manually or automatically by the fluid media delivery system 144. It will be understood that in this context, scrubbing media can be any material; liquid, solid or combinations thereof, which are being investigated to determine their ability to remove some material from a substrate.

The sample 106 is scrubbed, for example, for a set amount of time 507. The shaker table 110 is set, for example, at a predetermined rate and travel length. The force between the brushes 140 and samples can be set at a desirable weight, as discussed above. At the end of the predetermined time, which preferably is a period of time sufficient to produce enough material removal from at least one of the samples being tested and to distinguish between experimental variables across the samples, the samples are removed from the scrubber apparatus 102. The samples are allowed to dry 509. Two or more duplicate measurements can be performed for each sample.

The samples can then be imaged 511 as detailed above. The images thus produced are processed and analyzed to determine the extent of material removal from the various samples.

Figure 9:
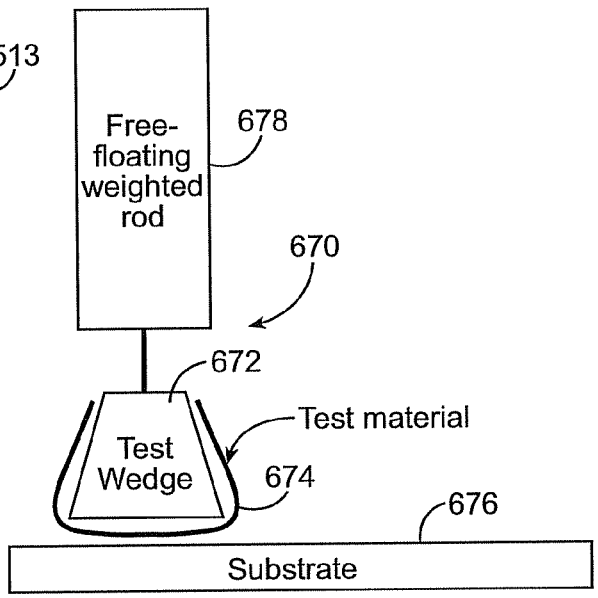
FIG. 9 shows another embodiment of a scrubbing device holder.

FIG. 9 shows yet another embodiment of a scrubbing device holder 670. The holder 670 allows the operator to mount flexible materials (cloth, leather, vinyl or paper, sandpaper, and the like) to the holder that would then be brought into contact with a substrate 676 in the same manner as a brush (see FIGS. 1 and 5, for example). The holder 670 preferably includes an upper body portion 678 which is of a desired weight or capable of being provided with sufficient weight for the test. The test material, for example, a fabric used in many consumer wiping applications, would be attached to a fastener end 672 of the holder. The materials 674 could be secured by any suitable means, for example, hook and loop fasteners, adhesives and the like. A formulation for testing is then applied to material 674 fastened to the fastener end 672 or deposited directly on the substrate 676. The test then proceeds in the same manner as detailed above, using the holder 670 in the same manner and position as a brush. The size and shape of the fastener end 672 could be altered depending on the test specifications and the material being attached thereto.

Figure 10:
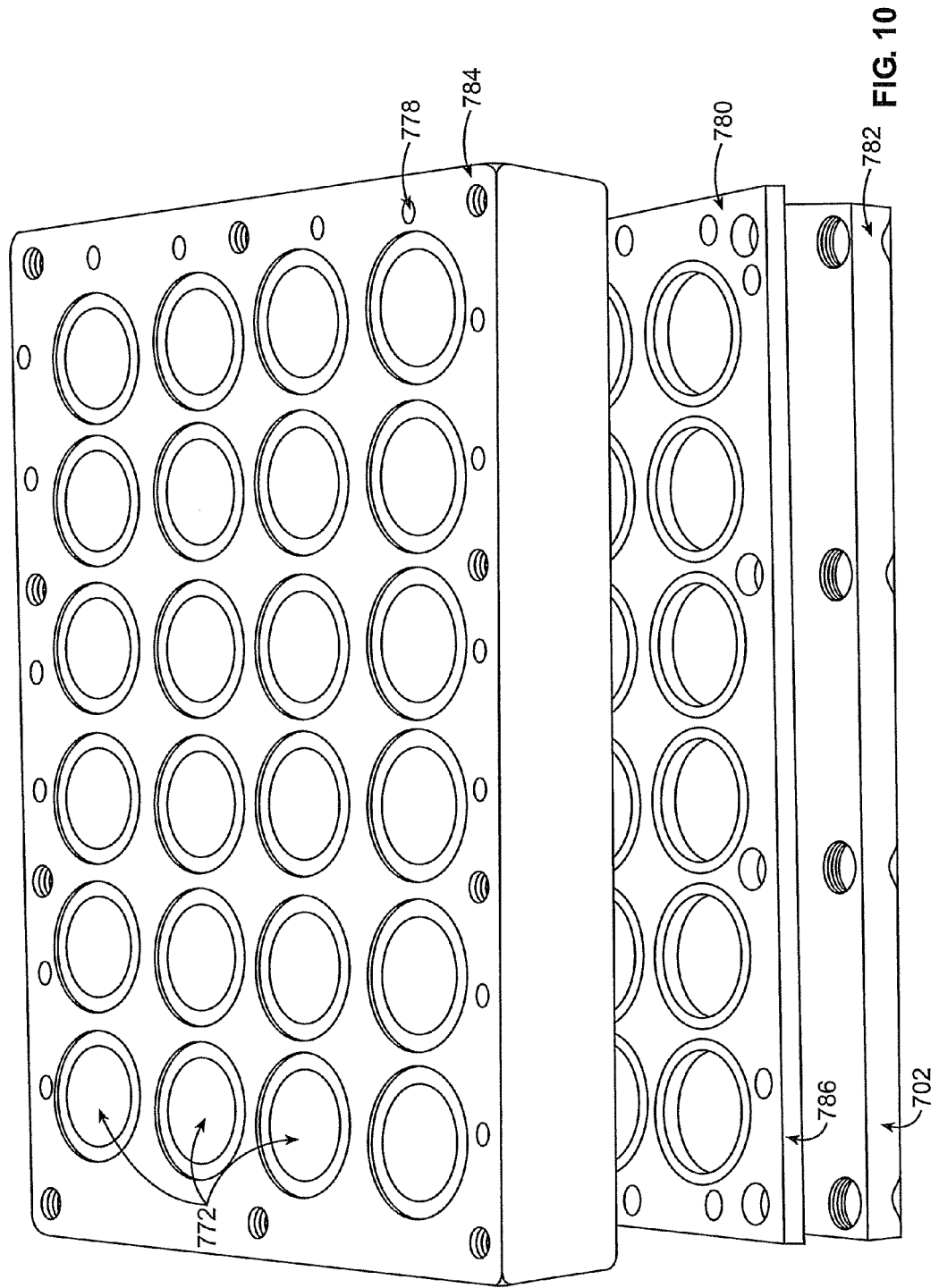
FIG. 10 shows an expanded perspective view of a scrub testing system according to a further embodiment of the invention.
Figure 11:
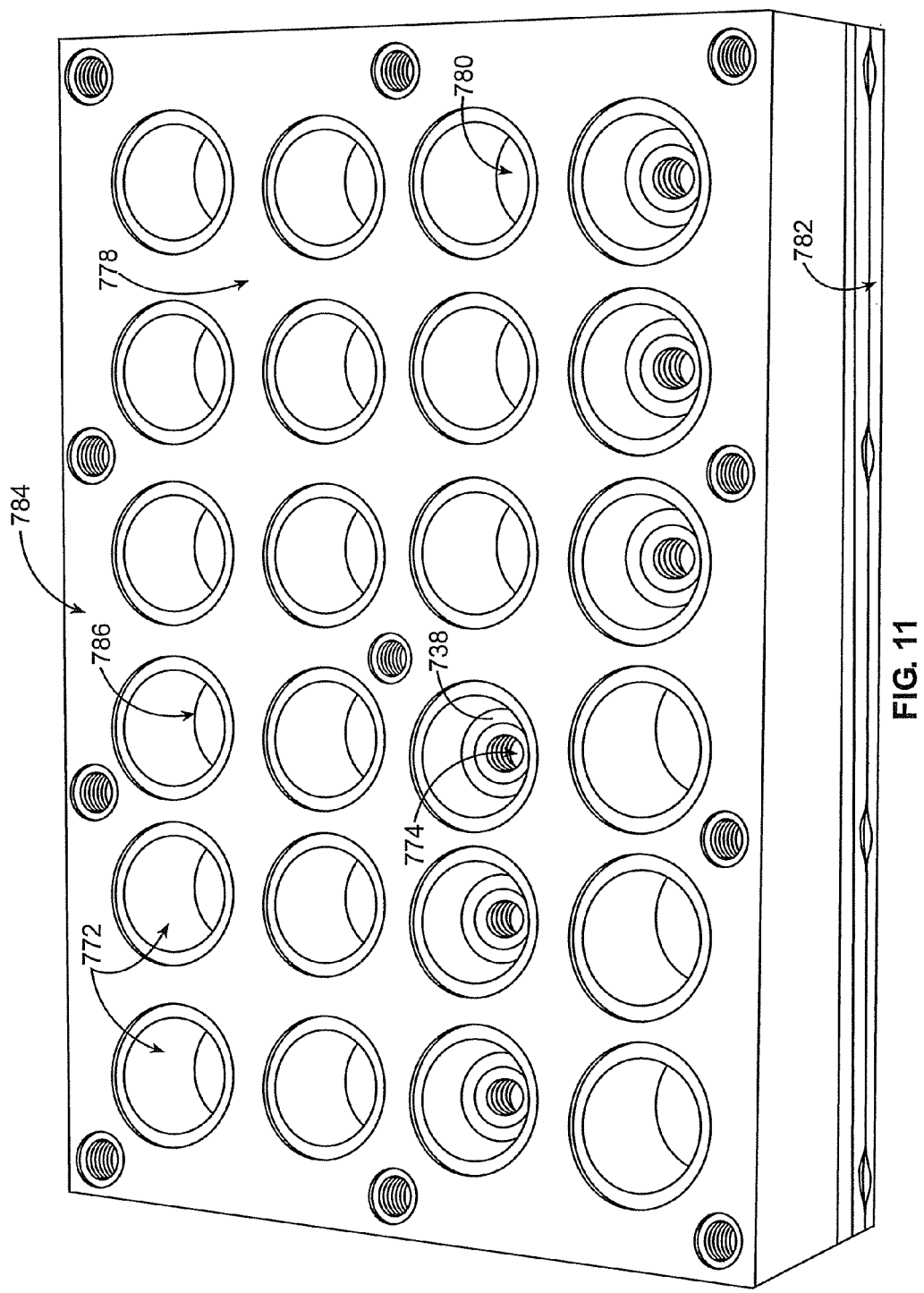
FIG. 11 shows a perspective view of the scrub testing system of FIG. 11 in an assembled state.
Figure 12:
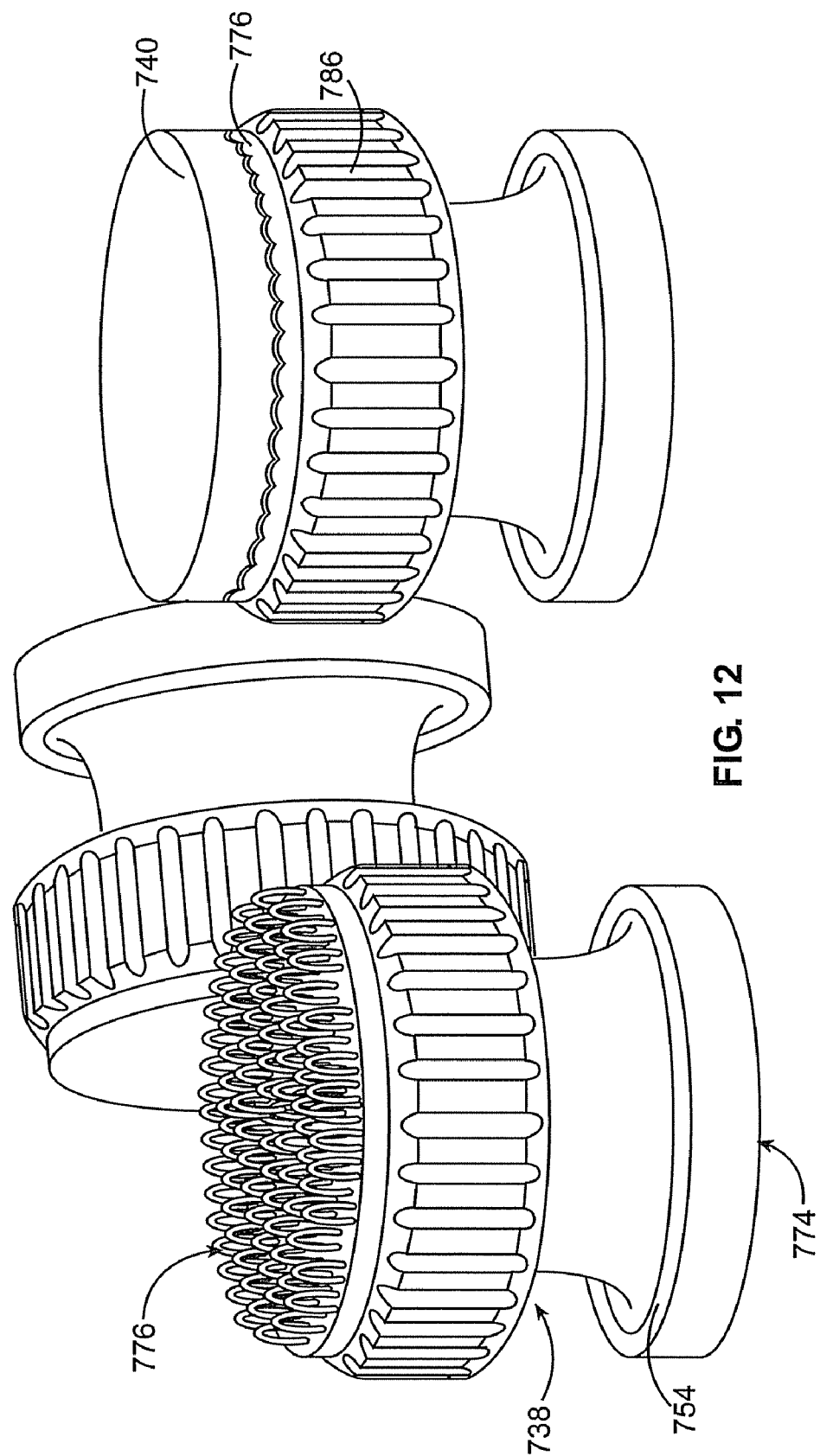
FIG. 12 shows yet another embodiment of a scrubbing device holder.

Referring to FIGS. 10-12, a parallel throughput scrubbing system 702 is shown which incorporates another embodiment of a scrub device holder 738. The scrub device holders 738 include weighted bodies 754, to impart mechanical energy to the test system. Each body 754 includes a receptacle 774 for receiving additional weight in a secure fashion. In the embodiment shown, the receptacle 774 is a threaded socket for receiving a threaded shaft (not shown) for receiving threaded weights (not shown). The body 754 also can include a knurled periphery 786 to contact a well 772 in order to cause the scrub device holders 738 to move in a desired fashion during testing.

In this embodiment, the scrubbing devices or brushes 740 are held in place by hook and loop material 776. In this manner, any material can be affixed to the holder 738 for testing. Each of the holders 738 are provided with a scrubbing device 740 and placed into a well 772 of a well block 778. The well block 778 is made of plastic, preferably having a self lubricating property, such as Teflon.

The well block 778 is positioned and fastened over a soiled substrate 780. The substrate 780 is disposed between the well block 778 and a metal base plate 782. The block 778, substrate 780 and base plate is fastened together, for example, by bolts, into a scrubber assembly 784.

The assembly 784 is fastened to a shaker (see FIG. 1) for processing. During movement, preferably orbital agitation, of the entire device, the scrub device holders 738 spin freely at an RPM consistent with the orbital shaker RPM. After a specific time interval, shaking is stopped, the scrub device holders 738 are removed and the substrate is examined and analyzed to determine the extent of cleaning.

As an example, a soiled substrate 780 (glass, ceramic, vinyl or metal) is bolted to a Teflon block 778 having 24 individual holes in it. The block 778 has an o-ring 786 for each hole or well 772 to reduce formulation leakage to adjacent wells. After bolting the base plate 782 to the Teflon block 778, a scrub device holder 738 is added to each well 772. Each scrub device holder 738 includes a metal weighted body 754, approximately 0.4" in diameter, to which a particular scrub material 740 is attached, usually by means of hook and loop fasteners. Examples of scrub material 740 can include sandpaper, paper, cloth, sponge, screen (plastic and metal), kitchen scrubbers and wipes. The scrub device holder 738 is placed into the well 772 and a desired volume of the intended test formulation is added (not shown). The assembly 784 is placed on an orbital shaker and agitated for a specified interval. The assembly 784 is removed, inverted and the test formulation drained out along with the test scrub device holder 738. The scrub device holder 738 can be retained for examination. The assembly 784 is disassembled and the substrate 780 examined to determine the extent of soil removal.

The embodiment of FIGS. 10-12 differs from the previous embodiments in that in the previous embodiment (FIG. 1) the brushes are held rigidly in the X-Y plane and allowed to move only along the Z-axis. Meanwhile, the substrate moves beneath the brushes to affect cleaning. In the present embodiment, the scrub device holders 738 float freely above the substrate with no constraints (except gravity) in any axis. Further, in the previous embodiment, the force on the brushes can be increased by adding mass to the interior of the brush holder. Increasing the mass for the scrub device holders 738 of the present embodiment can require changing to a different metal object. Finally, the previous embodiment is a self-contained device in that the sample is loaded into the unit which contains the brushes, substrate holder, shaker motor and possibly a mechanism to add liquid directly to the test sample.

Another example of a cleaning test using the embodiment 702 of FIGS. 10-12 can be considered an example of a cleaning experiment according to methods of the invention. A vinyl substrate 780 is cut to approximately 3.25"×5", and mounting holes 786 cut along the perimeter. The substrate 780 is then coated with synthetic kitchen grease incorporating a red pigment. The soil is allowed to age on the vinyl substrate 780 overnight at room temperature.

The next day the substrate is mounted to Teflon block 778 using 11 small bolts (not shown) which presses the substrate 780 between a solid metal base plate 782 and the Teflon block 778. The substrate 780 is positioned so that the soil is visible by looking into the individual wells 772. The Teflon block 778 is cut so that it contains 24 holes 772 in a 4×6 array. The holes 772 are about 0.6" in diameter and positioned apart 0.75" measured center-to-center. The holes 772 are notched (not shown) to accept an o-ring 786 to reduce leakage from the individual wells. Once mounted to the block 778 individual scrub device holder 738 having a mass about 50 g, are placed into each well 772. Finally, 120 uL of test formulation is added to each well 772 and the assembly 784 is transferred to an orbital shaker (not shown).

The shaker is set at 650 rpm and allowed to agitate the device for 3 minutes. At the end of that time, the assembly 784 is removed from the shaker and the scrub device holders 738 are removed from each well 772. Finally, the used formulation is removed from the wells 772, either by inversion into waste or aspiration to be saved for examination at a later time. Analysis of the formulation cleaning efficiency is made using digital image analysis of the substrate before and after processing as described herein.

Figure 13:
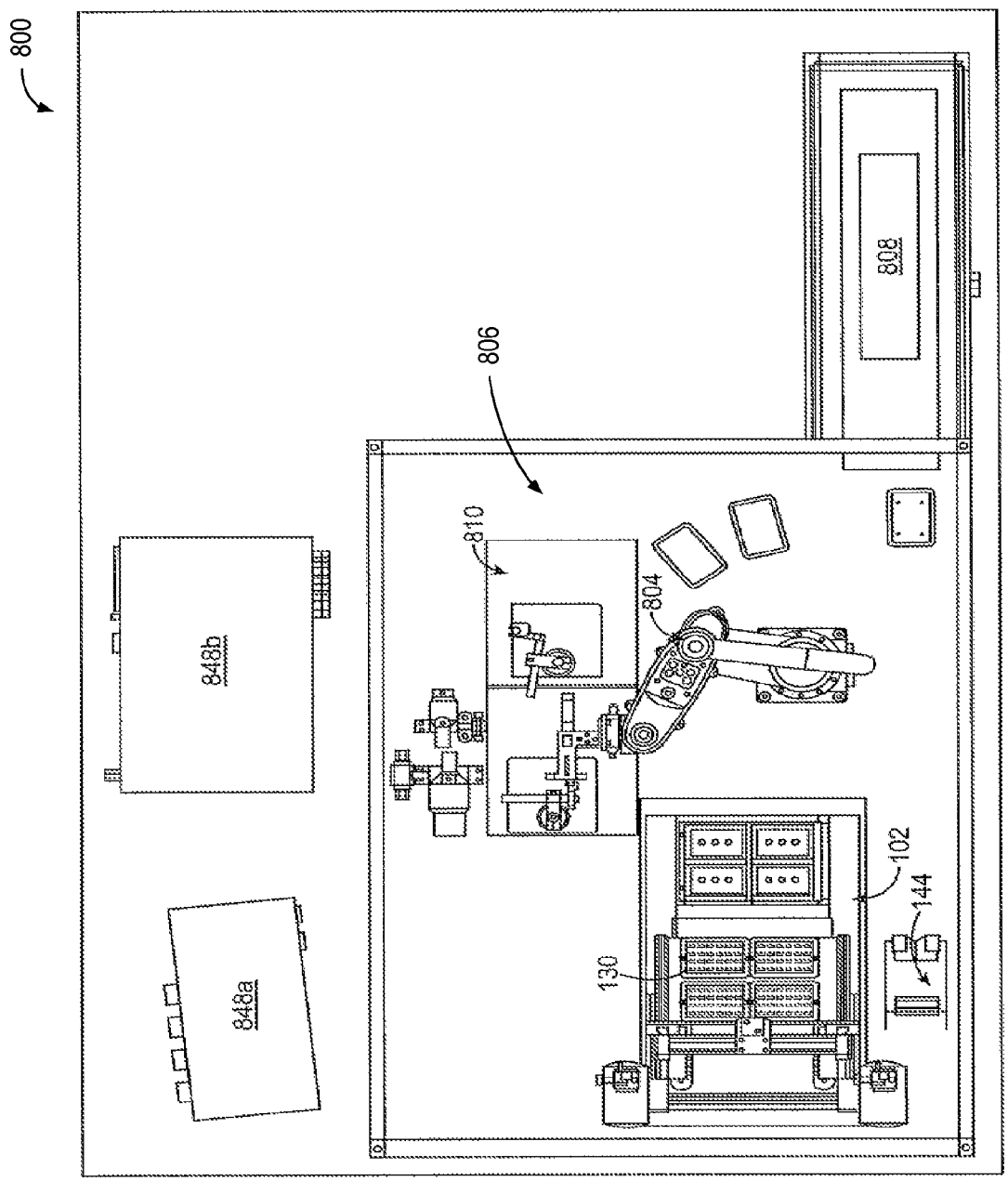
FIG. 13 shows an embodiment of a high throughput scrub testing system.

FIG. 13 shows a generalized schematic showing the main parts of a high throughput scrub testing system 800 according to an embodiment of the invention. The structure and function of each of the depicted elements is described herein or well known in the art.

Some elements of the system 800 are preferably fixed to a base 806, which is a structure holding various elements in place. The system 800 includes a scrubber assembly 102, as described herein and shown in FIG. 1, for example. The scrubber assembly is preferably fixed to the base 806. The system 800 includes a robot 804, for example an Epson E2S SCARA model. The robot 804 is fixed to the base 806. It will be understood that a number of automated robotic systems could be employed. The robot 804 performs movement of sample trays 130 (see FIG. 1) and potentially other elements of the system. In one example, the robot 804, loads and removes trays 130 automatically from a stacking system 804 into the scrubber assembly 102, transfers the trays from the scrubber assembly 102 to a washing and drying station 810, returns the washed trays to a stacking station 808 for drying, and in one embodiment conveys the dried trays to an imaging station (not shown).

A media dispensing station 144 is preferably positioned on the base 806 near the scrubber assembly 102. The media dispensing station 144 includes a syringe pump such as a New Era NE-501 syringe pump that contains a standard syringe and can be agitated to enable dispersions to remain dispersed. It will be understood that the robot 804, scrubber assembly 102 and the media dispensing station 144 will have associated controllers, represented herein by elements 848a and 848b, and a computer (not shown), as is known in the art.

Figure 14:
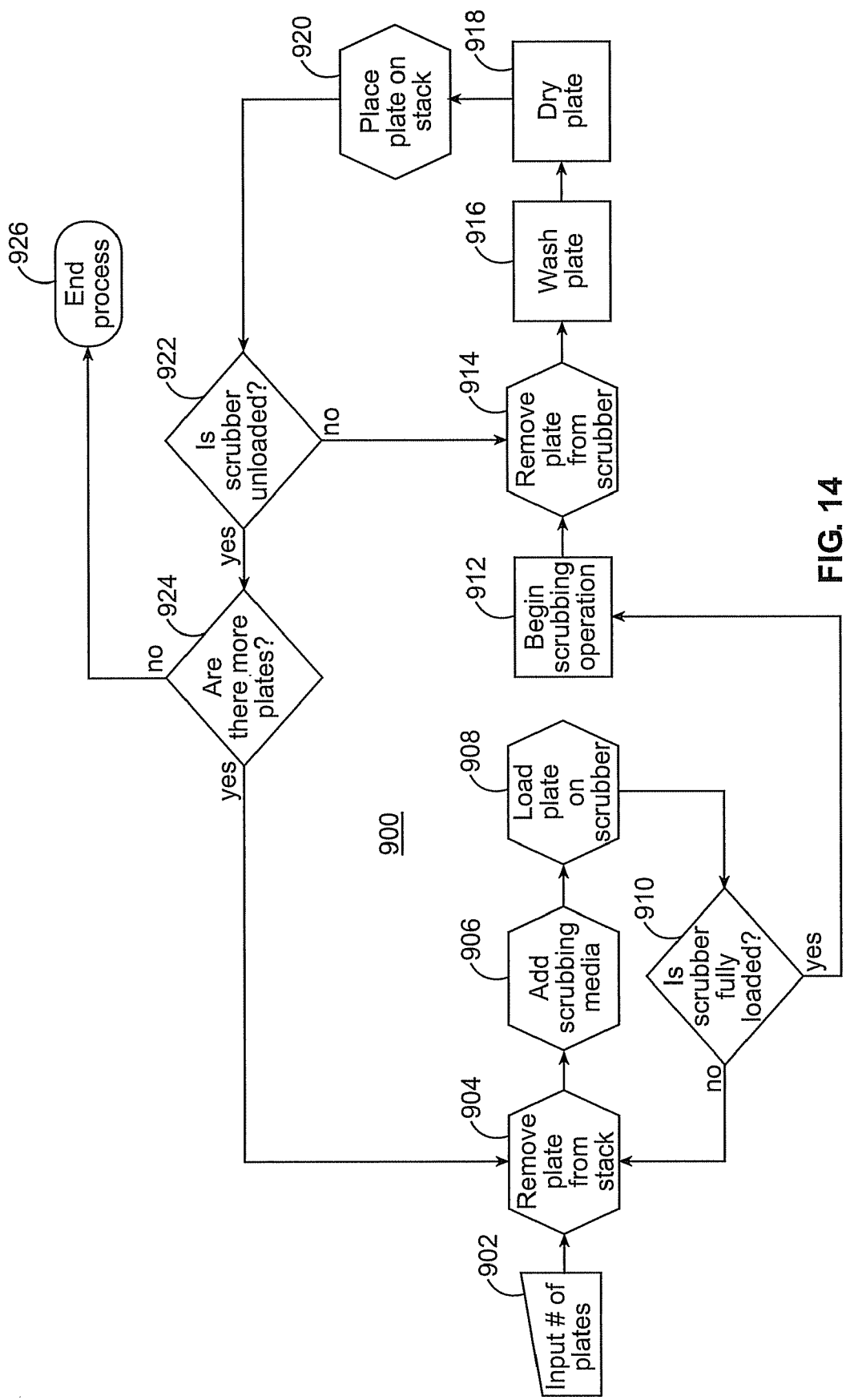
FIG. 14 shows a flowchart showing a method of operating a high throughput scrub testing system according to one embodiment of the invention.

FIG. 14 shows a flow chart with a method of operation of the system 800 shown in FIG. 13, according to an embodiment of the invention. The method 900, and referring to the previous figures and description, includes inputting into a computer the number 902 of trays 130 (plates) to be loaded onto the scrubber 102 for each run. The system robot 804 removes a first plate 904 from a source of plates. Scrubbing media is added 906 to the plate 130 at a media dispensing station 144. The plate 130 is loaded 908 onto an open position of the scrubber 102. The system 800 determines if the scrubber 102 is fully loaded 910. If not, the system 800 cycles back to step 904 until the scrubber is fully loaded, and when fully loaded, the system begins the scrubbing operation 912.

Upon completion of the scrubbing operation 912, a plate 130 is removed 914 from the scrubber 102. The removed plate 130 is washed 916 at a washing and drying station 810, and then dried 918. The plate 130 is transferred from the washing and drying station 810 to a plate stacking station 808 at step 920. The system 800 determines if the scrubber 102 has been unloaded 922. If the scrubber 102 has not been fully unloaded, the robot 804 retrieves another one of the scrubbed plates 130 and transfers it to the washing and drying station 810 at step 914 and repeats steps 916, 918 and 920 and 922.

The system 800 determines if there are more plates 130 to be scrubbed at step 924. If there are more plates 130 to be scrubbed, the method returns to step 904. Of there are no more plates 130, the process is ended at step 926.

To those skilled in the art to which this invention pertains, the above-described preferred embodiment can be subject to change or modification. Such change or modification can be carried out without departing from the scope of the invention, which is intended to be limited only by the scope of the appended claims.

What is claimed is:

1. A device for performing testing on a plurality of samples simultaneously, comprising:
 a scrubbing device array including a plurality of scrubbing devices;
 a sample stage for holding the plurality of samples in contact with the plurality of scrubbing devices; and
 a motion producing device for producing non-linear motion of the sample stage while the scrubbing device array is maintained in a fixed position, wherein the non-linear motion of the sample stage produces non-linear motion between the plurality of scrubbing devices and the plurality of samples in contact therewith.

2. The device of claim 1, further including a mechanism for providing a predetermined force to a scrubbing device.

3. The device of claim 2, wherein the mechanism includes one or more weights.

4. The device of claim 1, wherein the motion producing device is a shaker table.

5. The device of claim 1, wherein each of the plurality of scrubbing devices includes one or more of bristles, fabric or sheets of material, composite materials, plastic, rubber, blades, multi-blade devices, sandpaper, and abrasives incorporated onto or into a fabric.

6. The device of claim 1, wherein each of the plurality of scrubbing devices includes a brush.

7. The device of claim 6, wherein each of the brushes has a generally rectangular or round cross sectional shape.

8. The device of claim 1, wherein each of the scrubbing devices is sized and shaped to have a contact area from about 5% to about 75% of an area of each of the plurality of samples.

9. The device of claim 1, further including a plurality of scrub device holders corresponding to the number of scrubbing devices.

10. The device of claim 9, wherein each of the plurality of scrub device holders are adapted to be weighted.

11. The device of claim 9, wherein each of the plurality of scrub device holders are hollow for receiving one or more weights.

12. The device of claim 9, wherein the scrub device holders are held in the scrubbing device array and permitted to move vertically.

13. The device of claim 1, further includes a mechanism for delivering scrubbing media to each of the samples.

14. The device of claim 1, wherein the sample stage comprises at least one vacuum hold-down device for removably securing at least one sample.

* * * * *